United States Patent
Hyde et al.

(10) Patent No.: US 9,877,824 B2
(45) Date of Patent: Jan. 30, 2018

(54) INTRAOCULAR LENS SYSTEMS AND RELATED METHODS

(71) Applicant: ELWHA LLC, Bellevue, WA (US)

(72) Inventors: Roderick A. Hyde, Redmond, WA (US); John Marshall, Farnborough (GB); Clarence T. Tegreene, Mercer Island, WA (US); Roberto Zaldivar, Mendoza (AR); Roger Zaldivar, Mendoza (AR)

(73) Assignee: ELWHA LLC, Bellevue, WA (US)

( * ) Notice: Subject to any disclaimer, the term of this patent is extended or adjusted under 35 U.S.C. 154(b) by 0 days.

(21) Appl. No.: 14/807,673

(22) Filed: Jul. 23, 2015

(65) Prior Publication Data

US 2017/0020659 A1    Jan. 26, 2017

(51) Int. Cl.
*A61F 2/16* (2006.01)
*A61B 5/00* (2006.01)

(52) U.S. Cl.
CPC .......... *A61F 2/1627* (2013.01); *A61B 5/0031* (2013.01); *A61F 2250/0002* (2013.01)

(58) Field of Classification Search
CPC .... A61F 2/1656; A61F 2/1654; A61F 2/1648; A61F 2/1627; A61F 2/1624; A61F 2/1613
See application file for complete search history.

(56) References Cited

U.S. PATENT DOCUMENTS

| | | | |
|---|---|---|---|
| 5,066,301 A | 11/1991 | Wiley | |
| 5,108,429 A | 4/1992 | Wiley | |
| 5,171,266 A | 12/1992 | Wiley et al. | |
| 5,203,788 A | 4/1993 | Wiley | |
| 5,344,447 A | 9/1994 | Swanson | |
| 6,857,741 B2 | 2/2005 | Blum et al. | |
| 6,871,951 B2 | 3/2005 | Blum et al. | |
| 7,023,594 B2 | 4/2006 | Blum et al. | |
| 7,396,126 B2 | 7/2008 | Blum et al. | |
| 7,475,984 B2 | 1/2009 | Blum et al. | |
| 7,517,083 B2 | 4/2009 | Blum et al. | |
| 7,832,864 B2 | 11/2010 | Barrett et al. | |
| 8,446,341 B2 | 5/2013 | Amirparviz et al. | |
| 8,608,800 B2 | 12/2013 | Portney | |
| 8,885,139 B2 | 11/2014 | Peyghambarian et al. | |

(Continued)

FOREIGN PATENT DOCUMENTS

| | | | |
|---|---|---|---|
| WO | WO 2009/153764 A2 | 12/2009 | |
| WO | WO 2014/194432 A1 | 12/2014 | |
| WO | WO 2016135434 A1 * | 9/2016 | ........... G02F 1/1335 |

OTHER PUBLICATIONS

PCT International Search Report; International App. No. PCT/US2016/043062; Oct. 21, 2015; pp. 1-3.

(Continued)

*Primary Examiner* — David Isabella
*Assistant Examiner* — Dinah Baria
(74) *Attorney, Agent, or Firm* — Dorsey & Whitney LLP

(57) ABSTRACT

Embodiments disclosed herein are directed to intraocular lens systems having a plurality of materials therein, with at least some of the materials having a diffraction pattern therein and an electrically-modifiable index of refraction collectively configured to selectively alter the focal length of the intraocular lens system. Methods of modifying a focal length of an intraocular lens system are also disclosed.

57 Claims, 4 Drawing Sheets

(56) References Cited

U.S. PATENT DOCUMENTS

| | | |
|---|---|---|
| 2002/0140899 A1 | 10/2002 | Blum et al. |
| 2003/0210377 A1* | 11/2003 | Blum .................. G02B 27/017 351/159.4 |
| 2003/0231293 A1 | 12/2003 | Blum et al. |
| 2004/0027501 A1 | 2/2004 | Blum et al. |
| 2005/0140924 A1 | 6/2005 | Blum et al. |
| 2005/0270481 A1 | 12/2005 | Blum et al. |
| 2006/0098164 A1 | 5/2006 | Blum et al. |
| 2006/0164593 A1 | 7/2006 | Peyghambarian et al. |
| 2007/0121065 A1 | 5/2007 | Cox et al. |
| 2008/0106633 A1 | 5/2008 | Blum et al. |
| 2008/0208335 A1 | 8/2008 | Blum et al. |
| 2009/0009717 A1 | 1/2009 | Barrett et al. |
| 2009/0032679 A1 | 2/2009 | Holladay |
| 2009/0105817 A1 | 4/2009 | Bretthauer et al. |
| 2009/0195749 A1 | 8/2009 | Blum et al. |
| 2010/0001926 A1 | 1/2010 | Amirparviz et al. |
| 2010/0002190 A1 | 1/2010 | Clarke et al. |
| 2010/0324408 A1 | 12/2010 | Klink et al. |
| 2011/0025955 A1 | 2/2011 | Bos et al. |
| 2012/0140167 A1 | 6/2012 | Blum |
| 2013/0035760 A1 | 2/2013 | Portney |
| 2013/0073038 A1 | 3/2013 | Azar |
| 2013/0218270 A1 | 8/2013 | Blanckaert et al. |
| 2013/0222756 A1 | 8/2013 | Van Heugten |
| 2014/0085726 A1 | 3/2014 | Portney |
| 2014/0128941 A1 | 5/2014 | Williams |
| 2014/0132904 A1 | 5/2014 | Bos et al. |
| 2014/0156000 A1 | 6/2014 | Campin et al. |
| 2014/0240656 A1 | 8/2014 | Pugh et al. |
| 2015/0057748 A1 | 2/2015 | Azar |
| 2015/0205126 A1* | 7/2015 | Schowengerdt ... H04N 13/0468 345/633 |
| 2015/0362749 A1 | 12/2015 | Biederman et al. |

OTHER PUBLICATIONS

PCT International Search Report, International App. No. PCT/US2016/043065; Nov. 5, 2015; pp. 1-3.

PCT International Search Report; International App. No. PCT/US2016/043068; Oct. 12, 2016; pp. 1-4.

* cited by examiner

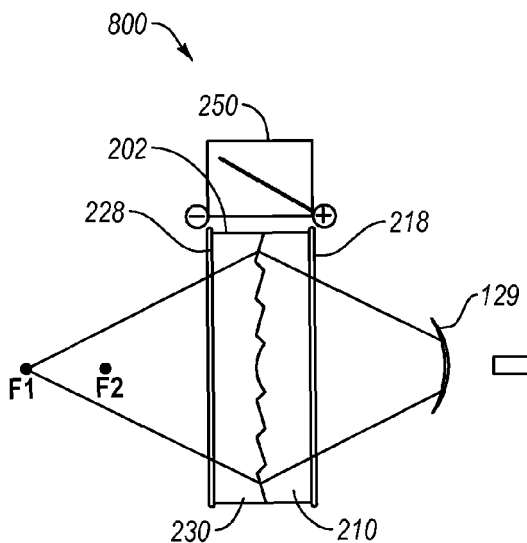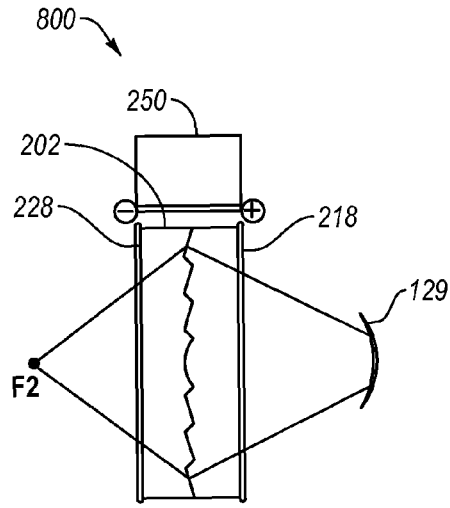
*FIG. 8A*  *FIG. 8B*
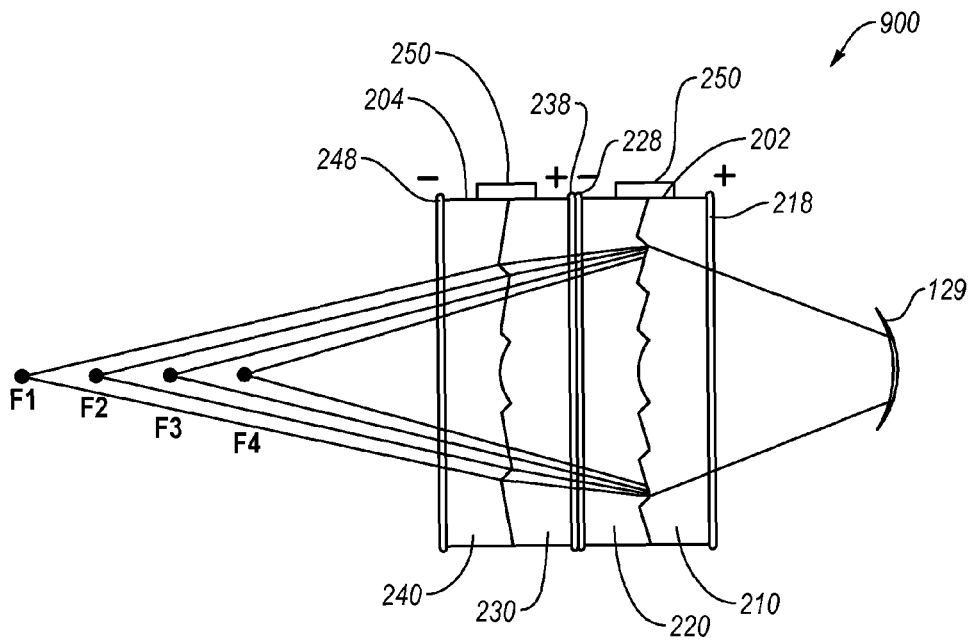
*FIG. 9*

INTRAOCULAR LENS SYSTEMS AND RELATED METHODS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Intraocular lenses ("IOLs"), such as pseudophakic IOLs, aphikic IOLs, or phakic IOLs ("PIOLS"), can be used to correct the vision of a subject. Typical IOLs can include monofocal, multifocal, or accommodative configurations. IOLs can include an optic element (e.g., lens) and haptic elements (e.g., arms or wings configured to aid in positioning the IOL).

Such configurations can be limited to focusing either on near or far vision without selectively modifiable adjustment therebetween. Therefore, manufacturers, users, and designers of IOLs continue to seek improved IOLs.

SUMMARY

Embodiments disclosed herein are directed to IOL systems having a plurality of materials therein, with at least some of the materials having a diffraction pattern and an electrically-modifiable index of refraction collectively configured to selectively alter a focal length of the IOL system. Methods of using such IOL systems are also disclosed.

In an embodiment, an IOL system is disclosed. The IOL system includes a diffractive lens configured to be implanted in an eye of a subject. The diffractive lens includes a first material having an electrically-modifiable first index of refraction, a first outer surface, and a first diffraction surface defining a first diffraction pattern; and a second material having a second index of refraction, a second outer surface remote from and generally opposing the first outer surface of the first material, and a second diffraction surface defining a second diffraction pattern. The second diffraction pattern is substantially complementary to the first diffraction pattern. The IOL system includes a first electrode disposed adjacent to the first outer surface of the first material and a second electrode disposed adjacent to the second outer surface of the second material. The IOL system further includes a controller including control electrical circuitry operably coupled to the first and second electrodes. The controller is configured to bias the first and second electrodes to modify at least the electrically-modifiable first index of refraction of the first material and a focal length of the IOL system.

In an embodiment, a method of modifying a focal length of an IOL is disclosed. The IOL includes a diffractive lens. The diffractive lens includes a first material having an electrically-modifiable first index of refraction, a first outer surface, and a first diffraction surface defining a first diffraction pattern; and a second material having a second index of refraction, a second outer surface remote from and generally opposing the first outer surface of the first material, and a second diffraction surface defining a second diffraction pattern. The second diffraction pattern is substantially complementary to the first diffraction pattern. The IOL further includes a first electrode disposed adjacent to the first outer surface of the first material and a second electrode disposed adjacent to the second outer surface of the second material. The IOL includes a controller including control electrical circuitry operably coupled to the first and second electrodes, the controller configured to bias the first and second electrodes to modify at least the electrically-modifiable index of refraction of the first material and a focal length of the diffractive lens. The method includes, via the controller, biasing the first and second electrodes to modify at least the electrically-modifiable first index of refraction of the first material and a focal length of the IOL.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 8A and 8B are schematic side, cross-sectional views of a portion of the diffractive lens of an IOL system before and after activation of the electro-optical material therein, according to an embodiment.

FIG. 9 is a schematic side, cross-sectional view of a portion of the diffractive lens of an IOL system having multiple focal lengths according to an embodiment.

DETAILED DESCRIPTION

Figure 1:
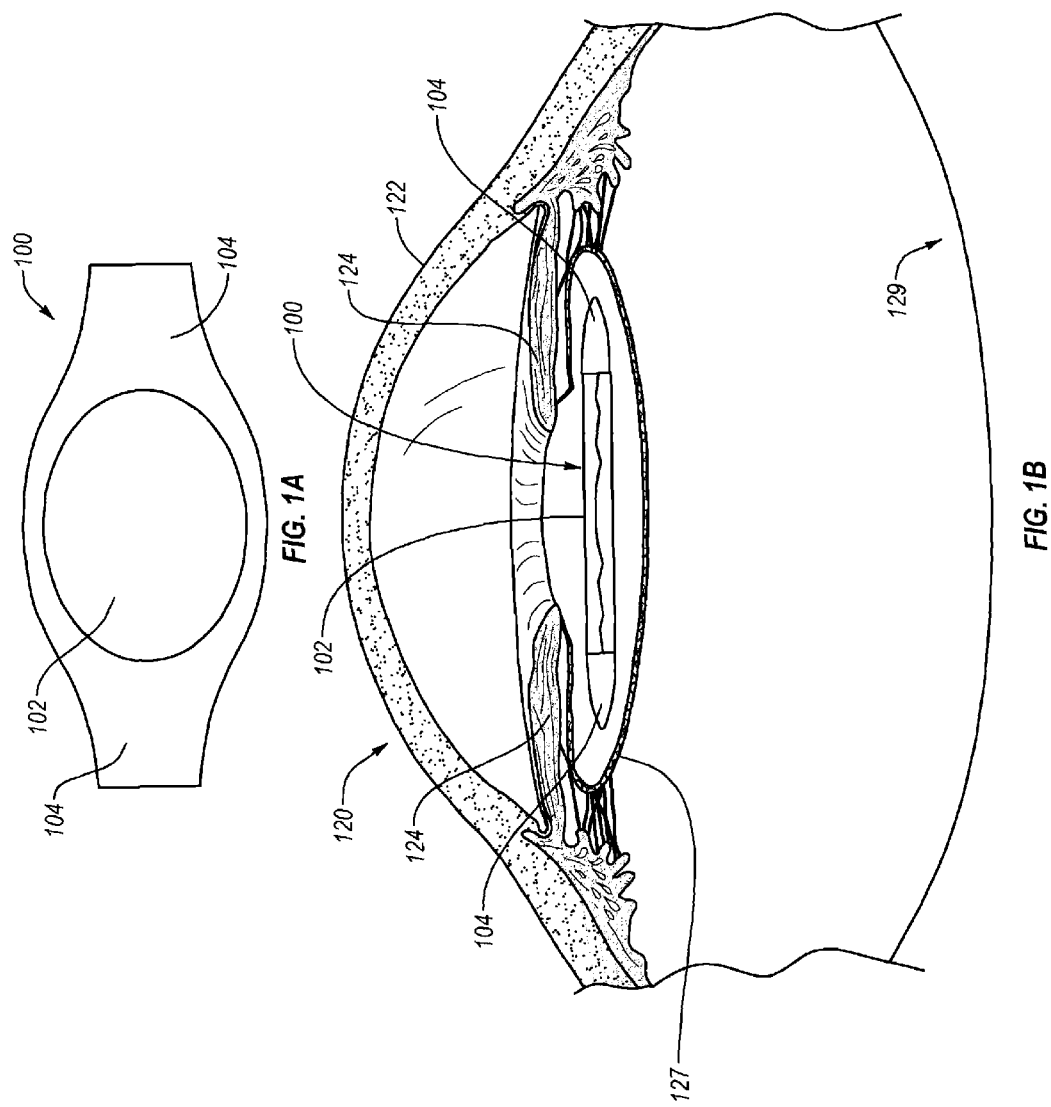
FIG. 1A is a top view of an IOL, according to an embodiment.
FIG. 1B is a side cross-sectional view of an eye having the IOL of FIG. 1A therein.

Embodiments disclosed herein are directed to IOL systems having a plurality of materials therein, with at least some of the materials having a diffraction pattern and an electrically-modifiable index of refraction collectively configured to selectively alter a focal length of the intraocular lens system. Methods of using such IOL systems are also disclosed.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The IOLs and systems disclosed herein can provide a selectively modifiable IOL having a selectively modifiable focal length. The IOLs disclosed herein can include a lens and one or more haptics. The lens can include at least one material having an electrically-modifiable index of refraction (including any birefringence associated therewith) and a diffraction surface defining a diffraction pattern therein. The IOLs disclosed herein can change focal length by applying a bias or voltage to the at least one material. An IOL can include a first material having an electrically-modifiable index of refraction and a diffraction surface defining a diffraction pattern. The IOL can include a second material having a substantially fixed index of refraction and a diffraction surface, or optionally, an electrically-modifiable index of refraction and a diffraction surface. The first and second materials can interface at their diffraction surfaces (which can be complementary and adjacent to each other), and the diffraction patterns in each are configured to focus light onto the retina of a subject from one or more specific focal lengths. The IOL can include a first electrode adjacent to, in, or on the outer surface of the first material and a second electrode adjacent to, in, or on the outer surface of the second material. The first and second electrodes can provide an electrical bias or voltage across the first and second materials effective to cause any electro-optical material therein to exhibit an altered or modified index of refraction. The modified index of refraction can cause the IOL to exhibit a different focal length, such as shorter or longer than the original or non-activated focal length of the IOL. Numerous embodiments are disclosed below, including IOLs having multiple selectively modifiable diffractive lenses, and combination refractive diffractive lens IOLs.

FIG. 1A is a top view of an IOL 100. The IOL 100 is configured to fit in or on one or more anatomical structures of the eye. The IOL 100 can include a lens 102 and one or more haptics 104. The one or more haptics 104 are physical structures attached to the IOL 100 that hold the IOL 100 in place within the capsular bag within the eye. The lens 102 can be configured to focus light onto the surface of the retina of a subject to improve or correct the vision of a subject. The lens 102 can be substantially circular or elliptical. The lens 102 can include, or be configured as, one or more of a diffractive lens and, optionally, further include a refractive lens. As discussed in more detail below, the lens 102 can be configured as a diffractive lens having a selectively modifiable index of refraction and focal length. The lens 102 can be configured to augment or correct visual deficiencies of a subject or to replace the lens of a subject, such as in cataract surgeries. As shown in FIG. 1A, haptics 104 can be configured as wings extending away from the lens 102. In an embodiment, the haptics 104 can be configured as arms or struts having an elbow or bend therein. The arms can be similar to the wings shown in FIG. 1A with one or more portions of the center of the wings removed therefrom.

FIG. 1B is a side, cross-sectional view of an eye 120 having the IOL 100 implanted therein. The eye 120 can include a cornea 122, an iris 124, a natural lens, and a retina 129 therebehind. One or more IOLs 100 can be implanted in the eye 120. The IOL 100 can be implanted over the natural lens, in front of (e.g., in the anterior chamber) or behind the iris 124 (e.g., in the posterior chamber), or internal to the natural lens such as in the capsular bag 127 of the natural lens. In an embodiment, the eye 120 may not include the natural lens. In such cases, the IOL 100 can replace the natural lens (e.g., can be placed in the anterior chamber, the posterior chamber, or internal to the capsular bag that is used to contain the natural lens). In an embodiment, the haptics 104 can be positioned on one or more structures in the eye 120. For example, the haptics 104 can be positioned on the ciliary body or muscles or in or on a capsular bag 127 of the natural lens. The lens 102 can be located laterally at approximately the midpoint (e.g., center) of the eye 120, with the haptics 104 extending laterally therefrom toward a periphery of the eye. The IOL 100 and, specifically the lens 102, can include one or more materials having a selectively modifiable index of refraction and a diffraction pattern therein. The lens 102 of the IOL 100 is discussed in more detail below.

Figure 2:
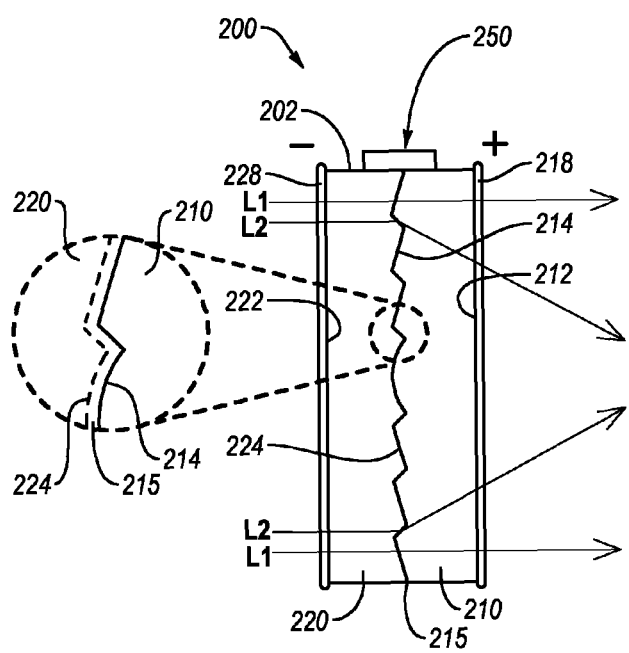
FIGS. 2-6 are side, cross-sectional views of portions of diffractive lenses of an IOL system according to various embodiments.

FIG. 2 is a side, cross-sectional side view of a portion a diffractive lens of an IOL system 200. The IOL system 200 can be used for cataract surgery, lens replacement, or vision augmentation or correction. The IOL system 200 can include a diffractive lens 202 and a controller 250. The diffractive lens 202 can include one or more materials therein, such as one or more electro-optical materials having an electrically-modifiable index of refraction. The controller 250 can be configured to selectively modify the index of refraction of one or more electro-optical materials in the IOL system 200.

The one or more materials can include a first material 210 and a second material 220. The first material 210 can include an electro-optical material. Electro-optical materials include those materials having an electrically-modifiable index of refraction. Electro-optical materials can be configured to provide a selectively modifiable index of refraction, such as a first, ground state index of refraction and at least a second, activated index of refraction induced by a stimulus (e.g., electrical stimulus applied to an electrically-modifiable material) applied thereto. In an embodiment, one or more electro-optical materials may each include a tunable (e.g., gradient) index of refraction over a specific voltage range, which can include a plurality of selectable focal lengths depending on the voltage applied. The second material 220 can include a substantially electro-optically inert material having a substantially fixed index of refraction. In an embodiment, the second material 220 can include an electro-optical material having a selectively modifiable index of refraction, similar to or different from the index of refraction of the first material 210. The first material can include a first outer surface 212 and the second material can include a second outer surface 222. The first and second outer surfaces 212 and 222 can be remote from one another and positioned in generally opposing directions (e.g., facing away from each other).

The first material 210 can include a first diffraction surface 214 generally opposite to the first outer surface 212 and defining a first diffraction pattern. The second material 220 can include a second diffraction surface 224 generally opposite to the second outer surface 222 and defining a second diffraction pattern. The second diffraction pattern can be substantially complementary (e.g., a mirror image of) to the first diffraction pattern such that the first and second diffraction surfaces 214 and 224 can be substantially seamlessly joined or mated together without any significant gaps therebetween. The first and second materials 210 and 220 can be joined at or meet at an interface 215 therebetween. The interface 215 can include an optically seamless diffraction pattern (e.g., the first and second diffraction patterns joined together) configured to focus light at a specific focal length or point relative to a subject onto a retina of the subject. In general, one fraction of incident light passing through the diffractive patterns will be focused to the specific focal length defined by the index of refraction of the material and diffractive patterns (e.g., defined by the fundamental diffractive order of the patterns), while a second fraction will be un-diffracted and proceed as though the diffractive patterns did not exist. Other (generally smaller) fractions of light will be diffracted to different focal lengths defined by the diffractive patterns (e.g., corresponding to negative or to higher diffractive orders). The relative fractions of incident light which are un-diffracted, diffracted to the specific focal length, and diffracted to the different focal lengths are determined by the depth of the diffraction surfaces and the index of refraction of their materials (e.g., for seamless complementary patterns, by the difference of the index of refraction of the first and second materials 210 and 220). In an embodiment, the first and second materials 210 and 220 may have the same index of refraction, resulting in substantially all incident light being un-diffracted. In an embodiment, the first and second materials 210 and 220 can have different indices of refraction, the value of which can be selected to result in substantially all incident light being diffracted to the specific focal length. Upon activation of the electro-optical material, the index of refraction can change to thereby change the effective focal length of the lens (e.g., to increase the fraction of incident light diffracted to the specific focal length rather than being un-diffracted) in conjunction with one or more diffraction patterns therein. For example, as shown in FIG. 2, the incident light L1 is not diffracted while the IOL system 200 is not activated (e.g., no electrical bias). While the IOL system 200 is activated (e.g., an electrical bias is applied) the incident light L2 can be diffracted due at least in part to the electrically modified index of refraction of one or more of the first and second materials 210 or 220. In an embodiment, one or more of the first and second materials 210 and 220 can include a tunable index of refraction based on the amount of voltage applied, which can cause the IOL system 200 having the same to exhibit a gradient of focusing power. For example, an IOL having at least one material having a tunable index of refraction can exhibit a first maximum focal length, a second minimum focal length, and a plurality of intermediate focal lengths therebetween, with each of the focal lengths based on the amount of voltage applied to the first and second electrodes 218 and 228. In such embodiments, a generally smooth graduation from a first focal length F1 to a second focal length F2 or a focal length therebetween can be established by gradually increasing or decreasing the electrical bias to the first and second electrodes 218 and 228 until the desired focal length is reached.

In order to provide a sufficient bias (e.g., an electrical voltage) to induce the modified index of refraction in the electro-optical material, the IOL system 200 can include a first electrode 218 and a second electrode 228. The first electrode 218 can be disposed adjacent to, in, or on the first outer surface 212 of the first material 210 and the second electrode 228 can be positioned adjacent to, in, or on the second outer surface 222 of the second material 220. The first and second electrodes 218 and 228 can be configured to deliver or maintain an electrical bias (e.g., electrical field, DC current, or low frequency AC current) across the first and second materials 210 and 220 effective to modify the index of refraction of one or both materials therebetween. Either of the first electrode 218 or the second electrode 228 can be configured as a positive terminal or a negative terminal with the remaining electrode being configured as the counterpart electrode.

The first and second electrodes 218 and 228 can be operably coupled to controller 250 by leads (not shown). As discussed in detail below, the controller 250 can include control electrical circuitry and a power source (e.g., battery) therein. The first and second electrodes 218 and 228 and the controller 250 can form a selectively controllable (e.g., selectively activated) circuit. The control electrical circuitry can be configured to direct the power source to bias the fists and second electrodes 218 and 228.

In an inactivated state, the electro-optical material can exhibit a first index of refraction and, when a bias is applied (e.g., in an activated state), the electro-optical material can exhibit a second or modified index of refraction, different from the first index of refraction. The effective focal point or length of the diffractive lens 202 incorporating the same can be similarly modified. For example, the diffraction patterns of diffractive lens 202 can be configured to provide a number of different focal lengths corresponding to different diffractive orders (e.g., for un-diffracted light, for the fundamental diffractive order or, for other diffractive orders, such as negative or higher diffractive orders). The relative amount of incident light delivered into each different focal length can be dependent upon the index of refraction of the electro-optical material (e.g., whether it is in an inactivated or activated state). For example, when a stronger focus (e.g., near focus) is desired, a bias can be applied across the diffractive lens 202 to modify the index of refraction of one of the first or second materials 210 or 220 therein to provide a focal length nearer the subject than the first focal length associated with the first index of refraction. In an embodiment, the focal length of the diffractive lens 202 (e.g., electro-optical material) without a bias applied thereto is greater than the focal length of the diffractive lens having a bias applied thereto. For example, in a first state embodiment, the first and second materials 210 and 220 have a substantially identical or identical index of refraction. In the first state, the IOL system 200 acts as a single lens having such index of refraction. Incident light is not further deflected by the diffraction pattern. In a second state embodiment, an electrical charge or bias is applied to the IOL system 200 and the index of refraction of the first material 210 is changed. In the second state embodiment, incident light is deflected at the diffraction pattern according to the difference in refractive indices of the first and second materials 210 and 220.

In an embodiment, (e.g., when IOL system 200 also includes a refractive lens or due to corneal focusing) diffractive lens 202 is not the only focusing element in the eye, so that light un-diffracted by the diffraction patterns will be delivered to one focal length (e.g., corresponding to a far focus), while light diffracted at either the fundamental diffractive order or one of the other diffractive orders will be delivered to a second focal length (e.g., corresponding to a near focus).

One or both of the first or second materials 210 or 220 can include an electro-optical material therein. The electro-optical material can be a solid state material or a liquid crystal material. The electro-optical material can be substantially transparent to visible wavelength light. In an embodiment, the electro-optical material can at least partially filter one or more wavelengths of light, such as one or more wavelengths of visible light. Suitable electro-optical materials can include at least one of lithium niobate, lithium tantalate, lead zirconate titanate, potassium dihydrogen phosphate, cadmium telluride, perovskite lead lanthanum zirconate titanate (PLZT), lead magnesium niobate-lead titanate (PMN-PT) (e.g., $Pb(Mg_{1/3}Nb_{2/3})O_3$—$PbTiO_3$ (PMN-PT)), mixtures of any of the foregoing, or any other suitable substantially transparent material having an electrically-modifiable index of refraction.

The second material 220 can include a substantially electro-optically inert material (e.g., having a substantially fixed index of refraction), such as glass; plastic; or other lens materials including one or more of polymethyl methacrylate (PMMA), polypropylene, silicone, polyvinyl fluoride (PVDF), polyamide, polyimide, hydrophobic acrylics, hydrophilic acrylics, combinations of the foregoing, or any other transparent material suitable for use in an IOL. In an embodiment, the first material 210 includes one or more substantially electro-optically inert materials therein. In an embodiment, each of the first material 210 and the second material 220 includes an electro-optical material such as any of those describe above. In an embodiment, one or both of the first material 210 or the second material 220 includes a solid state or a liquid crystal electro-optical material therein.

In an embodiment, neither the electrode 218 or electrode 228 are located at diffractive surfaces 214 or 224. Instead, for example, the electrode 218 and electrode 228 are located near outer surfaces 212 and 222, respectively. In such an embodiment, the electric field present throughout the first and second materials 210 and 220 can be more uniform (in strength, location, or direction) than in embodiments in which one of the electrodes 218 or 228 is located near the diffractive surface 214 or 224. In an embodiment, this uniformity can be utilized when a solid state electro-optic material is used for first material 210 or second material 220. In such embodiments, this electrode configuration can enable the diffractive lens to use solid state materials in a linear portion of their index-vs-field response curve, as opposed to use of liquid crystal materials in a saturated index-vs-field regime. In an embodiment, the second material 220 is selected so that its DC dielectric constant substantially matches the DC dielectric constant of first material 210, so that the thickness and slope variations caused by the interface between diffractive surfaces 214 and 224 do not cause substantial local variations in the electric field's uniformity (and hence in the refractive index of electro-optically active material 210 or 220).

The diffraction patterns of the first and second diffraction surfaces 214 and 224 can be configured to focus or converge the light from a specific focal length onto the retina of a subject without inducing significant interference (e.g., at the prismatic effect) at the retina. The diffraction pattern (e.g., diffraction grating or lens, digitally or continuously brazed profile) can be formed in one or both of the first material 210 or the second material 220 first, with the second material 220 or first material 210 being molded thereto or therein. For example, the diffraction pattern can be formed in the first material 210 and the second material 220 can be poured/molded onto the first material so that the second material 220 substantially conforms or is complementary to the diffraction pattern in the first material 210. The diffraction pattern can be defined by a spatial variation in a thickness of one or both of the first or second materials 210 or 220. In an embodiment, the changing the spatial variation in the thickness of one or both of the first or second materials 210 or 220 can provide or eliminate apodization in the images focused therethrough. In an embodiment, an apodized or unapodized spatial variation in the thickness of one or more materials can be used. In an embodiment, both of the first diffraction surface 214 and the second diffraction surface 224 can have the corresponding or complementary diffraction patterns formed therein (e.g., each having a pattern exhibiting substantially identical spatial periodicity), and the first and second materials 210 and 220 are fitted together to form a substantially unitary lens structure. In an embodiment, the first diffraction surface 214 and the second diffraction surface 224 can have different diffraction patterns (e.g., exhibiting substantially different spatial periodicity) formed therein, and the first and second materials 210 and 220 include another material therebetween having complementary surface configurations to the diffraction patterns (e.g., forming an interface having substantially identical spatial periodicity to each individual diffraction surface) in the first diffraction surface 214 and the second diffraction surface 224. The first material 210, the second material 220, and the another material can fit substantially seamlessly together to form a substantially unitary lens structure. Suitable diffraction patterns can include a Fresnel pattern (e.g., defining a Fresnel lens), a linear pattern (e.g., defining a diffraction grating), or any other pattern suitable for inducing diffraction (e.g., lens combined with grating, lens with aberrational corrections, etc.). Suitable diffraction patterns can include any number of steps therein, such as 10 or more, about 10 to about 1000, about 50 to about 500, about 100 to about 300, about 20 to about 250, or less than about 500 steps. The steps can include a step height of at least about 0.2 µm, such as about 0.5 µm to about 20 µm, 1 µm to about 10 µm, or less than about 50 µm. The step height, multiplied by the refractive index jump across the step (e.g., the index difference between the first material 210 and the second material 220) can define one wavelength of light (e.g., 550 nm) or multiple wavelengths. The steps can include a step length (e.g., diffractive period) of at least about 0.5 µm, such as about 1 µm to about 100 µm, about 5 µm to about 50 µm, about 1 µm to about 10 µm, or less than about 200 µm, the value being dependent upon the desired focal length and the number of wavelengths defined by the step height. The step profile or variation of step height versus lateral distance within each step length can be digitally or continuously blazed. Digitally blazed profiles can include a single step within each period, or multiple steps (e.g., 4 sub-steps of different step heights); while continuously blazed profiles can be linear ramps ("sawtooth" profiles), sections of parabolas, or other shapes.

The average axial thickness of the first or second materials 210 or 220 can vary depending on the materials used, the desired refractive or diffractive properties of the lens, the desired correction to the vision of a subject, or any other suitable criteria. The average thickness (e.g., including any ridges or grating) of the first or second material 210 or 220 can be at least about 0.5 µm, such as about 1 µm to about 3 mm, about 100 µm to about 2 µm, about 500 µm to about 1 mm, about 250 µm to about 2 µm, or about 1.5 mm. The average thickness of the first and second materials 210 and 220 can be identical or substantially different. In an embodiment, one or more portions of one or more of the first and second materials 210 or 220 can be substantially planar. For example, the first outer surface 212 and the second outer surface 222 can be substantially planar, such as in parallel to one another. As discussed in more detail below, one or more portions of the first and second materials 210 and 220 can be substantially non-planar (e.g., curved) and parallel or non-parallel to each other. In an embodiment where the first and second materials 210 and 220 include at least one non-parallel curved surface, the curvature of the non-parallel surfaces can form a refractive lens.

The first and second electrodes 218 and 228 can be configured to limit distortion of the visual quality of the IOL system 200 at the retina. For example, one or both of the first and second electrodes 218 and 228 can include a material substantially transparent to one or more wavelengths of visible light (e.g., substantially transparent to all visible light) or can be sufficiently thin to substantially limit any refractive or diffractive effects therefrom. In an embodiment, one or both of the first or second electrodes 218 or 228 can include a transparent conducting material. Suitable transparent conducting materials can include one or more of indium-tin-oxide; aluminum-doped zinc-oxide; indium-doped cadmium-oxide; or a transparent conductive polymer such as poly(3,4-ethylenedioxythiophene), Poly(3,4-ethylenedioxythiophene):poly(styrene sulfonate), or Poly(4,4-dioctylcyclopentadithiophene). In an embodiment, the first and second electrodes 218 and 228 can be about 0.05 µm thick or more, such as about 0.05 µm to about 500 µm, about 0.1 µm to about 200 µm, about 0.5 µm to about 100 µm, about 1 µm to about 50 µm, about 0.05 g to about 100 µm, about 1 µm to about 500 µm, or about 10 µm thick.

The first and second electrodes 218 and 228 can be configured to complement the surface geometry of one or more surfaces of the first and second materials 210 and 220. For example, one or both of the first and second electrodes 218 or 228 can be configured as substantially planar or curved to match the first outer surface 212 or the second outer surface 222.

In an embodiment, the overall or maximum thickness of the IOL system 200, including the diffractive lens 202 and the electrodes 218 and 228, can be at least about 10 µm. For example, the overall or maximum thickness can be about 10 µm to about 6 mm, about 500 µm to about 5 mm, about 100 µm to about 1.5 mm, about 250 µm to about 3 mm, about 1 mm to about 4 mm, about 3 mm to about 5 mm, about 4.5 mm to about 5.5 mm, about 2 mm, about 3 mm, or about 4 mm.

In an embodiment, the diffractive lens 202 of the IOL system 200 can be configured as a Fresnel lens having surface geometry configured to provide a sharp image to the retina (e.g., imaging Fresnel lens). The Fresnel lens can provide relatively greater optical and physical thickness than other types of diffractive lenses such as, corresponding to a high-order (e.g., $5^{th}$ order, $10^{th}$ order, $20^{th}$ order, etc.) diffraction profile and hence a greater number-of-optical-wavelengths of thickness. In an embodiment, the first material 210 can be configured as a Fresnel lens and the second material 220 can be configured with a substantially complementary surface to interface therewith. The first material 210 (e.g., Fresnel lens) or in some cases, the second material 220, may be each be formed from an electro-optical material or a substantially inert material, which may have a substantially similar or identical dielectric constant to allow substantially uniform voltage across the entire lens 202. In an embodiment, the first material 210 can include a first electro-optical material and the second material 220 can include a second electro-optical material having identical or different indices of refraction or dielectric constants. Depending on the diffraction blazing and geometric patterning of the Fresnel lens, the IOL may exhibit a series of potential focal lengths substantially in a gradient with the effective focal length dependent upon the amount of electrical bias thereacross. For example, when an electro-optical material formed as a Fresnel lens includes a sufficient blazing and geometric patterning, the IOL system 200 may be able to focus different orders of light onto the retina of a subject, thereby allowing a substantially continually graduating focal length dependent upon the amount of voltage applied across the electro-optical material.

Figure 3:
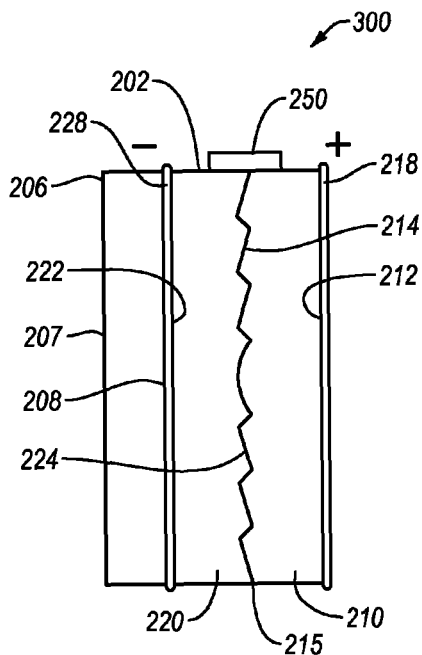

FIG. 3 is a side, cross-sectional view of a portion of a lens of an IOL system 300 according to an embodiment. The IOL system 300 can be configured substantially identical or similar to the IOL system 200, with like parts having like numbering. The IOL system 300 can include the diffractive lens 202 and a refractive optical element 206 (e.g., refractive lens) associated with and positioned optically in series with the diffractive lens 202. The refractive optical element 206 can comprise the second material as employed in the diffractive lens 202, or can comprise another optical material. The IOL system 300 includes the first material 210 and the second material 220. The first material 210 and the second material 220 include the first outer surface 212 and the first diffraction surface 214, and the second outer surface 222 and the second diffraction surface 224, respectively. The IOL system 300 includes the first electrode 218 and second electrode 228. The IOL system 300 further includes the controller 250 operably coupled to the first and second electrodes 218 and 228. The IOL system 300 can include a refractive optical element 206 (e.g., refractive lens) in series with the diffractive lens 202. For example, as shown in FIG. 3, the refractive optical element 206 can be in series with the diffractive lens 202 and positioned adjacent to the second outer surface 222 of the second material 220. The refractive optical element 206 can include one or more surfaces, such as outer surface 207 and interfacing surface 208.

The interfacing surface 208 can interface with the diffractive lens 202 adjacent to the second outer surface 222. The interfacing surface 208 can have a complementary configuration (e.g., parallel) to the second outer surface 222, such that the interfacing surface 208 remains in contact with the second outer surface 222 across substantially the entire second outer surface 222. In an embodiment, the interfacing surface 208 can interface with the diffractive lens 202 at the second electrode 228 (e.g., the second electrode 228 is interposed between the interfacing surface 208 and the second outer surface 222). In an embodiment, the interfacing surface 208 can interface with the diffractive lens 202 at the second outer surface 222, and the second electrode 228 can be disposed adjacent to the outer surface 207 of the refractive optical element 206.

The outer surface can 207 be substantially parallel to the interfacing surface 208 or can exhibit a non-parallel curvature resulting in a desired refraction. In an embodiment, one or both of the outer surface 207 or the interfacing surface 208 can exhibit a curvature (e.g., concave or convex). The curvature of one or both of the outer surface 207 or the interfacing surface 208 can be substantially parallel or non-parallel to each other, resulting in a desired refraction.

The curvature of one or both of the outer surface 207 or the interfacing surface 208 can be substantially parallel or non-parallel to one or more surfaces of the diffractive lens 202, resulting in a desired refraction. In an embodiment, the second material 220 can be at least partially configured as a refractive lens (e.g., having a curvature configured to refract light in a selected manner). In such embodiments, the second electrode 228 can be disposed adjacent to a surface of the refractively configured second material 220. As used herein, "curved" or "curvature" in conjunction with materials having a diffractive surface therein includes the average thickness of a material over the periodicity of any diffraction patterns therein (e.g., curvature does not include fine-scale peaks and valleys of the diffraction pattern).

In an embodiment, the refractive optical element 206 can be disposed adjacent to the first outer surface 212 of the first material 210 in a similar or identical manner as described above with respect to the second outer surface 222 of the second material 220. In an embodiment, more than one refractive optical element 206 can be disposed adjacent to the diffractive lens 202. For example, the one or more refractive optical elements 206 can be positioned optically in series with the diffractive lens 202 adjacent to the first outer surface 212 and the second outer surface 222. The one or more refractive optical elements 206 can include an electro-optical material or an electro-optically inert material therein. For example, the refractive optical element 206 can include an electro-optically inert material therein (e.g., an electro-optically inert material employed as the second material 220 of the diffractive lens 202), such that the refractive optical element 206 has a substantially fixed index of refraction.

In an embodiment, the refractive optical element 206 can be interposed between the first material 210 and the second material 220. The refractive optical element 206 can include diffraction patterns generally matching the first diffraction pattern and the second diffraction pattern such that the refractive optical element 206 can be substantially seamlessly interposed between the first and second materials. The refractive optical element 206 interposed between first and second materials 210 and 220 can be an electrically conductive material or an electrically insulative material. In an embodiment, the refractive optical element 206 can serve as an electrical insulator such that a bias applied to the first and second electrodes 218 and 222 adjacent thereto also extends through the refractive optical element. In an embodiment, the refractive optical element 206 having an electrically conducting material can be configured to serve as an electrode, such as the first electrode 218 or second electrode 228. The refractive optical element 206 interposed between the first and second elements 210 and 220 can have curved surfaces matching those curves of the surfaces to which they are adjacent. The refractive optical element 206 interposed between first and second materials 210 and 220 can have curved surfaces of slightly different curvatures forming a refractive lens.

The controller 250 can be used to apply a bias to the first and second electrodes 218 and 228 sufficient to alter the index of refraction of one or more of the first material 210, the second material 220, or in an embodiment, the refractive optical element 206.

Figure 4:
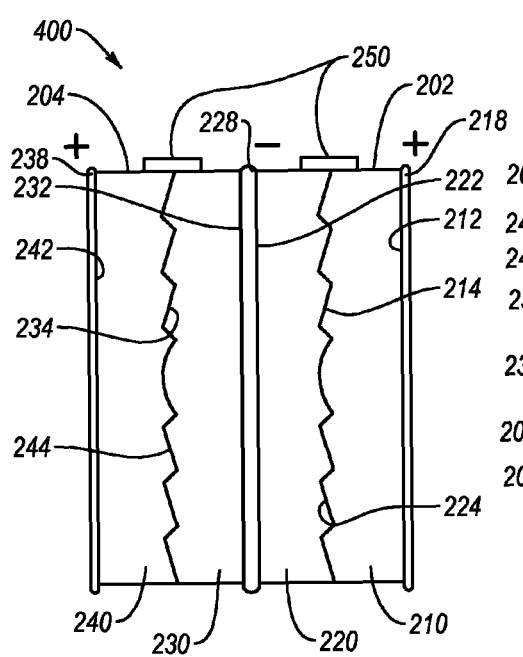

In an embodiment, a diffractive lens system can include a first diffractive lens and at least one additional diffractive lens similar to or different from the first diffractive lens. FIG. 4 is a side, cross-sectional view of a portion of a lens of an IOL system 400 according to an embodiment. The IOL system 400 includes a first diffractive lens 202, a second diffractive lens 204 in optical series with the first diffractive lens 202, and one or more controllers 250 configured to apply an electrical bias thereto. The first diffractive lens 202 can be similar or identical to the diffractive lens described above with respect to FIG. 2, including any components thereof. For example, the first diffractive lens 202 can include the first material 210 having the first outer surface 212 and the first diffraction surface 214; the second material 220 having the second outer surface 222 and the second diffraction surface 224; the first electrode 218 adjacent to the first outer surface 212; the second electrode 228 adjacent to the second outer surface 222; and the controller 250 configured to apply a bias therebetween, substantially as described above. The IOL system 400 can further include a second diffractive lens 204, such as in series with the first diffractive lens 202. The second diffractive lens 204 can include one or more components similar or identical to the components of the first diffractive lens 202.

The second diffractive lens 204 can include a third material 230 and a fourth material 240. The third material 230 can include a third outer surface 232 and a third diffraction surface 234 substantially opposite thereto and defining a third diffraction pattern. The fourth material 240 can include a fourth outer surface 242 and a fourth diffraction surface 244 substantially opposite thereto and defining a fourth diffraction pattern. The fourth diffraction pattern can be substantially complementary to the third diffraction pattern such that the third and fourth diffraction surfaces 234 and 244 are joined they have a substantially seamless (e.g., no gaps or voids) interface therebetween.

The second diffractive lens 204 can include one or more electrodes operably connected thereto. For example, the diffractive lens 204 can be operably coupled to one of the first electrode 218 such as when the fourth outer surface 242 is adjacent to the first outer surface 212, or, as shown, to the second electrode 228 such as when the third outer surface 232 is adjacent to the second outer surface 222. The second diffractive lens 204 can include one or more electrodes distinct from the first and second electrodes. For example, the second diffractive lens 204 can include a third electrode 238 disposed on or adjacent to the fourth outer surface 242. The third electrode 238 can include a material, configuration, thickness, or placement similar or identical to those described above for the first and second electrodes 218 and 228. For example, the third electrode 238 can include a transparent conductive material configured to limit any effect on the transmission of light therethrough.

In an embodiment, the third material 230 can include identical or similar material compositions, diffraction patterns, thicknesses, or any other characteristic of the first material 210 described herein. In an embodiment, the fourth material 240 can include identical or similar material compositions, diffraction patterns, thicknesses, or any other characteristic of the second material 220 described herein. For example, the third material 230 can include an electro-optical material and the fourth material 240 can include an electro-optically inert material or an electro-optical material as disclosed above with respect to the first and second materials 210 and 220.

The third material 230 or fourth material 240 can be configured differently than the first and second materials 210 and 220 respectively. In an embodiment, the third and fourth materials 230 and 240 can include a material composition, diffraction pattern, thickness, or any other characteristic different from the first and second materials 210 and 220. For example, the third and fourth materials 230 and 240 can include a diffraction pattern different from the first and second materials 210 and 220, such that application of an electrical bias across the third and fourth materials 230 and 240 results in a different focal length for the IOL system 400 than a bias applied across the first and second materials 210 and 220.

In an embodiment, the index of refraction of each of the first, second, third, and fourth materials 210-240 can be same or different than one or more of the other first, second, third, and fourth materials 210-240. For example, the electro-optical material of the first material 210 can have a different electrically-modifiable index of refraction than the electro-optical material of the third material 230, in one or more of the ground and activated states. In an embodiment, the third and fourth materials 230 and 240 can include an electro-optical material or electro-optically inert material having a different index of refraction than the first and second materials 210 and 220, such that application of an electrical bias across the third and fourth materials 230 and 240 results in a different focal length for the IOL system 400 than a bias applied across the first and second materials 210 and 220.

The IOL system 400 can include one or more controllers 250 operably coupled to the first electrode 218, the second electrode 228, or the third electrode 238. In an embodiment, a first controller 250 can be operably coupled to the first electrode 218 and the second electrode 228, either directly or indirectly through electrical leads (not shown). The first controller 250 can include a power supply and control electrical circuitry configured to direct the power source to apply an electrical bias between the first and second electrodes 218 and 228 sufficient to alter the index or refraction of any electro-optical material (e.g., first material 210) therebetween. In an embodiment, the second diffractive lens 204 can be disposed adjacent to the second outer surface 222, as shown. In an embodiment, a second controller 250 can be operably coupled to the second electrode 228 and the third electrode 238 either directly or indirectly through electrical leads (not shown). The second controller 250 can include a power supply and control electrical circuitry configured to direct the power source to apply an electrical bias between the second and third electrodes 228 and 238 sufficient to alter the index or refraction of any electro-optical material therebetween (e.g., the third material 230). In such an embodiment, the first and second controllers 250 can each be operably coupled to the second electrode 228 but be configured as separate circuits each including the first and third electrodes 218 and 238, respectively, and each capable of being operated independently by each controller 250.

In an embodiment (not shown), the second diffractive lens 204 can be disposed adjacent to the first outer surface 212. In such an embodiment, the first controller 250 can be similar or identical as described above and the second controller 250 can be operably coupled to the first electrode 218 and the third electrode 238 either directly or indirectly through electrical leads. The second controller 250 can include a power supply and control electrical circuitry configured to direct the power source to apply an electrical bias between the second and third electrodes 228 and 238 sufficient to alter the index or refraction of any electro-optical material therebetween (e.g., the third material 230). In such an embodiment, the first and second controllers 250 can each be operably coupled to the first electrode 218 but be configured as separate circuits each including the second and third electrodes 228 and 238, respectively, and each capable of being operated independently by each controller 250. The controllers 250 can be operated independently to selectively alter the index of refraction of one or more electro-optical materials in the IOL system 400 to provide one or more differing focal lengths thereto. While depicted as having more than one controller 250, the IOL system 400 can be configured with only one controller 250 operably coupled to each of the first, second, and third electrodes 218-238. In such embodiments, the single controller 250 can be configured to independently operate the first and second electrodes 218 and 228, and the first and third electrodes 218 and 238 or second and third electrodes 228 or 238 depending on the series arrangement of the first diffractive lens 202 and the second diffractive lens 204.

Figure 5:
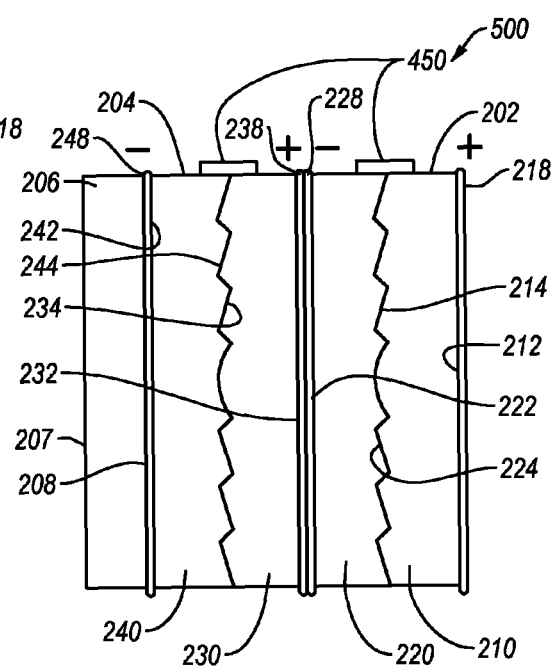

In an embodiment, rather than sharing one or more electrodes between adjacent diffractive lenses as described above with respect to IOL system 400, an IOL can include can include a fourth electrode operably coupled to the second diffractive lens. FIG. 5 is a side, cross-sectional view of an IOL system 500 having four electrodes forming two separate circuits, according to an embodiment. In an embodiment, the first and second electrodes 218 and 228 can be operably coupled to the first and second outer surfaces 212 and 222 of the first and second materials 210 and 220. In an embodiment, the IOL system 500 can include a third electrode 238 and a fourth electrode 248 operably coupled to the third and fourth outer surfaces 232 and 242 of the third and fourth materials 230 and 240, respectively.

The third or fourth electrodes 238 or 248 can be configured similar or identical to the first and second electrodes 218 or 228, including any material, thickness, position, or other property described herein. For example, the third and fourth electrodes can be configured as be a thin layer of an electrically conductive transparent material matching the contours of the surface to which it is attached. In an embodiment, the third and fourth electrodes 238 and 248 can be parallel to each other. In an embodiment, the third and fourth electrodes 238 and 248 can be configured to differ from the first and second electrodes 218 and 228 by one or more of any material, thickness, position, or other property associated therewith. In an embodiment, the first electrode 218 and the third electrode 238 can be configured as positive electrodes and the second electrode 228 and the fourth electrode 248 can be configured as negative electrodes, or vice versa. In an embodiment, a transparent insulating material can be disposed between the second and third electrodes 228 and 238 or the first and fourth electrodes 228 and 248 when positioned adjacent to one another. The transparent insulating material can limit or prevent electrical leakage between the electrodes and unwanted partial activation of the electro-optical materials associated with the electrode not being selectively activated. Suitable transparent insulating material can include acrylic or polycarbonate materials.

The first and second electrodes 218 and 228 can be operably coupled to a controller 250 and the third and fourth electrodes can be operably coupled to a controller 250, such as the same controller 250 or a separate controller 250. The controller 250 can be configured to selectively operate the first and second electrodes 218 and 228 and the third and fourth electrodes 238 and 248 to independently provide an electrical bias sufficient to alter the electrically-modifiable index of refraction of a material therebetween (e.g., the third material 230) and the focal length of the IOL system 500.

In an embodiment, one or more refractive optical elements (e.g., refractive lens) can be positioned optically in series with one or more diffractive lenses. FIG. 5 is a side, cross-sectional view of a lens of the IOL system 500 having diffractive lenses 202 and 204 as described above with respect to IOL system 400 and further including the refractive optical element 206 in series therewith. The refractive optical element 206 of the IOL system 500 can be similar or identical to the refractive optical element described above with respect to IOL system 300. For example, the refractive optical element 206 can include a material separate and distinct from the first, second, third, or fourth materials 210-240. The refractive optical element 206 can include a material such as an electro-optical material or an electro-optically inert material. The refractive optical element 206 can be positioned in series with the first and second diffractive lenses 202 and 204 adjacent to the fourth outer surface 242 as shown, adjacent to the first outer surface 212, or interposed between the first and second lenses 202 and 204. In such an embodiment, the outer surface 207 of the refractive optical material 206 can be disposed adjacent to the second or third outer surface 222 or 232 of the second or third materials 210 or 220 and the interfacing surface 208 can be disposed adjacent to the other of the second or third outer surface 222 or 232. In an embodiment, more than one refractive optical element 206 can be disposed in series with more than one diffractive lens. In an embodiment, the first diffractive lens 202 can be configured with a first curve and the second diffractive element can be planar or have a different curvature than the first curve. One or more of the surfaces 207 or 208 of the refractive optical element 206 associated therewith can be curved or planar to match the surface geometry of one or more of the surfaces of the diffractive lenses adjacent thereto. In an embodiment, the refractive optical element 206 can include differing curvatures on the outer surface 207 and the interfacing surface 208 such that the refractive optical element 206 provides and additional refractive property to the IOL system associated therewith. In an embodiment, the refractive optical element can include one or more of the first, second, third, or fourth materials 210-240. For example, one or more of the first, second, third, or fourth materials 210-240 can include a curved outer surface or a curved diffraction surface, resulting in refraction.

Figure 6:
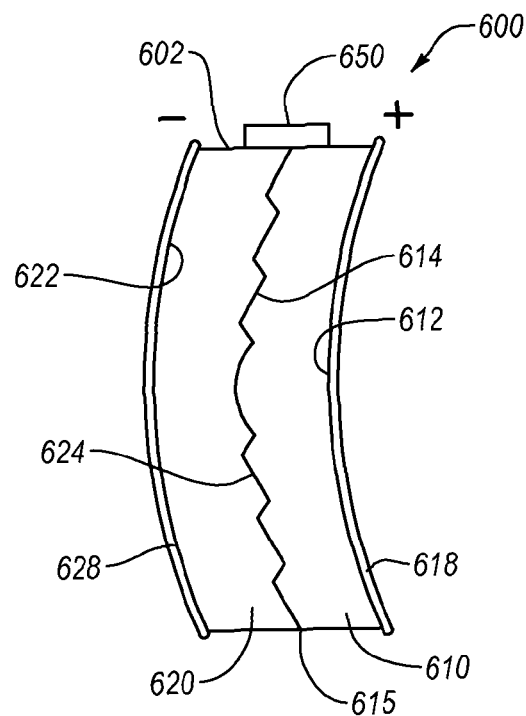

FIG. 6 is a side, cross-sectional view of a portion of a lens of an IOL system 600 having a curved diffractive lens 602, according to an embodiment. The IOL system 600 can be configured substantially identical or similarly as the IOL system 200, with like parts having like numbering. For example, the IOL system 600 can include a diffractive lens 602 and a controller 650. The diffractive lens 602 can be similar or identical to the diffractive lens 202 or 204 described above, including any components or properties thereof. For example, the diffractive lens 602 can include the first material 610 having the first outer surface 612 and the first diffraction surface 614; the second material 620 having the second outer surface 622 and the second diffraction surface 624; the first electrode 618 adjacent to the first outer surface 612; the second electrode 628 adjacent to the second outer surface 622; and the controller 650 configured to apply a bias therebetween, substantially as described above. One or more of the first material 610, first outer surface 612, first diffraction surface 614, the second material 620, second outer surface 622, and second diffraction surface 624, the first electrode 618; the second electrode 628, or the controller 650 can be configured or have one or more properties similar or identical to the corresponding, diffractive lens 202, first material 210, first outer surface 212, first diffraction surface 214, the second material 220, second outer surface 222, and second diffraction surface 224, the first electrode 218, the second electrode 228, and the controller 250 described above.

The diffractive lens 602 can include the first material 610 having a first outer surface 612 and a first diffraction surface 614. One or more of the first outer surface 612 or first diffraction surface 614 can include a curvature therein. The diffraction pattern in the diffraction surface of the materials having curved surfaces can be configured to diffract light in concert with the curved configuration. In an embodiment, the curvature of the first outer surface 612 can be similar or identical to the curvature of the first diffraction surface 614 (e.g., the averaged curvature of the first diffraction surface ignoring the peaks and valleys of the diffraction pattern therein) such that the first material causes light passing therethrough to bend at least partially based on the curvature therein. For example, the curvature of the first outer surface 612 can be substantially parallel to the curvature of the first diffraction surface 614. In an embodiment, the curvature of the first outer surface 612 can be different than the curvature of the first diffraction surface 614 such that the first material 610 causes light passing therethrough to refract at least partially based on each of the curvatures therein.

The second material 620 can include a second outer surface 622 and a second diffraction surface 624. One or more of the second outer surface 622 or second diffraction surface 624 can include a curvature therein. In an embodiment, the curvature of the second outer surface 622 can be similar or identical to the curvature of the second diffraction surface 624 (e.g., the average curvature of the second diffraction surface ignoring the peaks and valleys of the diffraction pattern therein). For example, the curvature of the second outer surface 622 can be substantially parallel to the curvature of the second diffraction surface 624. In an embodiment, the curvature of the second outer surface 622 can be different than the curvature of the second diffraction surface 624 such that the second material 620 causes light passing therethrough to refract at least partially based on the curvature therein. In an embodiment, the curvature of the second outer surface 622 can be different than the curvature of the first outer surface 612 such that the first material 610 and the second material 620 causes light passing therethrough to refract at least partially based on the curvature therein. In an embodiment in which diffractive lens 602 includes non-parallel surfaces (e.g., the outer surfaces 622 and 612, the first material surfaces 612 and 614, and/or the second material surfaces 622 and 624) such that light passing therethrough is at least partially refractive, diffractive lens 602 has both diffractive and refractive optical power and can function as a joint refractive-diffractive lens.

In an embodiment, one or more of the first outer surface 612, the first diffraction surface 614, the second outer surface 622, or the second diffraction surface 624, can include any one of a planar configuration, a concave curve, a convex curve, a compound concave or convex curve, or combinations thereof. For example, as shown, the first outer surface 612 can exhibit a concave curve, the second outer surface can exhibit a convex curve therein, the first diffraction surface 614 can exhibit a convex curve therein, and the second diffraction surface 624 can exhibit a concave curve therein. In an embodiment, the curvature of the first outer surface 612 can be similar or identical to the curvature of the second outer surface 622, such as substantially parallel thereacross. In an embodiment, the convex curvature of the first outer surface 612 can be slightly different from the convex curvature of the second outer surface 622 and configured to provide specific bend (e.g., focal length) to the light passing therethrough.

In an embodiment, the curvature of the first outer surface 612 can be different from the curvature of the second outer surface 622, thereby forming a refractive lens. For example, the first outer surface 612 can include convex curvature and the second outer surface 622 can include a convex curvature different from the first outer surface 612, a concave curvature, or planar configuration. In an embodiment, any surface of the first material 610 or the second material 620 can exhibit a different or identical geometry to one or more of the other surfaces of the first material 610 or the second material 620.

In an embodiment, the curvature of the first diffraction surface 614 (e.g., average curvature of the material ignoring any peaks or valleys of the periodicity therein) can be substantially complementary to the curvature of the second diffraction surface 624 such that the first and second diffraction surfaces fit seamlessly together to form a unitary lens at an interface 615 therebetween. In an embodiment, the curvature of the first diffraction surface 614 can be non-complementary to the curvature of the second diffraction surface 624 such that an intermediate material may be between the first and second diffraction surfaces to provide in interface 615 sufficient to create a seamless unitary lens.

In an embodiment, the first and second electrodes 618 and 628 can include a geometry configured to match the surface on which they are disposed. For example and as shown, the first electrode 618 can have a concave curvature corresponding to the concave curvature of the first outer surface 612 and the second electrode 628 can have a convex curvature corresponding to the convex curvature of the second outer surface 622.

In an embodiment, an IOL system can include an additional diffractive lens having a one or more surfaces including surface geometry (e.g., curvature or planar configurations) complementary, similar, or identical to the first outer surface, second outer surface, first diffraction surface, or second diffraction surface disclosed above. In an embodiment, the first lens can be configured as a refractive lens and the second lens can be configured as a refractive lens, each having a complementary or slightly different curvature therein. The first diffractive lens can have a different curvature from the second diffractive lens such that the combination of the first and second diffractive lenses creates a refractive optical element or lens.

Figure 7:
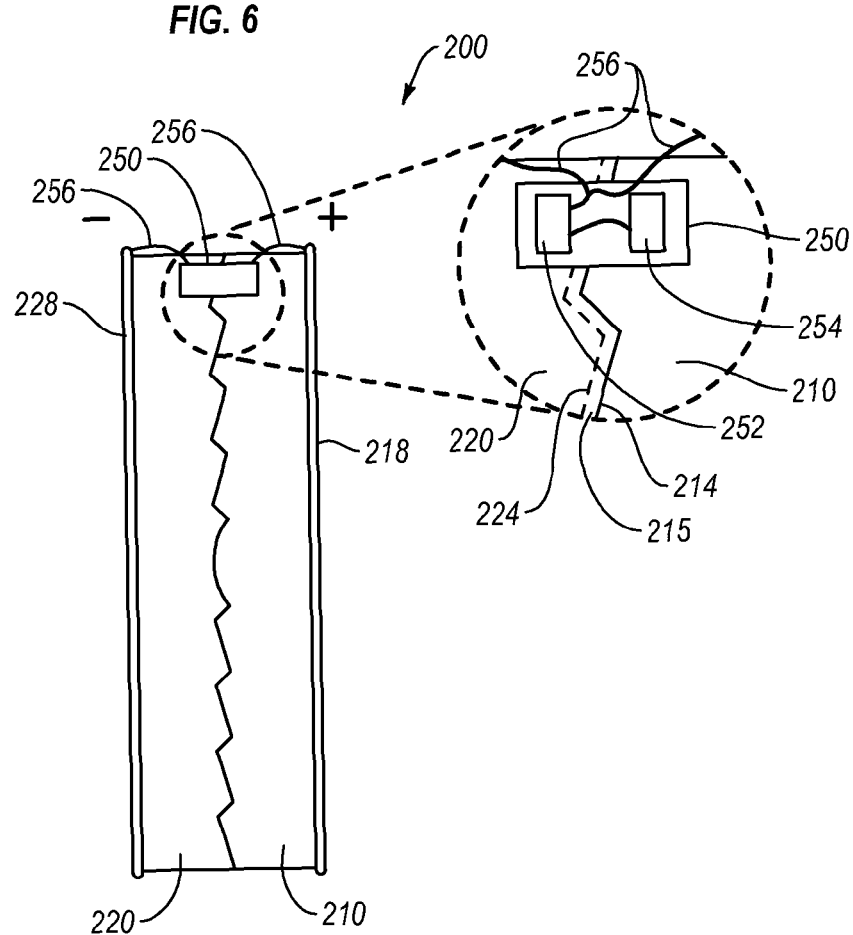
FIG. 7 is a cross-sectional side view of a portion of the diffractive lens of an IOL system including a schematic diagram of a controller associated therewith, according to an embodiment.

FIG. 7 is a side, cross-sectional view of a portion of a lens of the IOL system 200 including a schematic view of the controller 250, according to an embodiment. The controller 250 can be disposed within one or more of the haptic or the lens of an IOL. In an embodiment, the controller 250 can be at least partially embedded within the lens 202 of the IOL system 200. The controller 250 can include a power source 252 and control electrical circuitry 254 operably coupled thereto. The control electrical circuitry 254 can be configured to direct the power source 252 to apply a bias or voltage to one or more electrodes operably coupled thereto. The one or more electrodes can be operably coupled to the controller 250 or the power source 252 via one or more electrical leads 256. The electrical leads 256 can be at least partially embedded within the diffractive lens 202 or the haptic of an IOL. The controller 250 or the electrical leads 256 can be disposed at a periphery of the diffractive lens 204 or IOL so as not to interfere with the vision of a subject. The controller 250 or the electrical leads 256 can be positioned within one or more cavities formed in the interfacing surfaces of the first and second materials 210 or 220. In an embodiment, the controller 250 or the electrical leads 256 can be disposed entirely within one of the first material 210 or the second material 220, such as embedded within one or more cavities therein. In an embodiment, one or more of the controller 250, the power source 252, the control electrical circuitry, or the electrical leads 256 can be disposed externally to the diffractive lens such as on a surface thereof, or on an electrode associated therewith. In an embodiment, the electrical leads or the controller can be encased in a transparent insulating material (e.g., acrylic or polycarbonate) configured to prevent electrical leakage therefrom.

In an embodiment, the power source 252 can be configured to deliver an electrical bias to one or more electrodes or one or more circuits including one or more electrodes in each. For example, the power source 252 can be operably connected to a switch or gate configured to close a circuit having the first and second electrodes 218 and 228 therein. In an embodiment, the power source 252 can include a micro-battery or any other battery having a suitably small enough size to be able to fit into the IOL system 200. Suitable batteries can include a thin film battery, a button cell battery, or any other miniaturized battery. A suitable thin film battery can include a flexible thin film lithium-ion battery, such as the LiTe*STAR™ thin-film rechargeable battery or Thinergy® battery by Infinite Power Solutions, or equivalents thereof. The battery can be configured to deliver 0.1 mV or more, such as about 0.1 mV to about 20 V, about 0.5 mV to about 5 V, about 0.5 V, about 1 V, about 2 V, or about 10 V or less. The battery can be configured to deliver 0.1 mA or more, such as about 0.1 mA to about 1 A, about 0.2 mA to about 0.5 mA, or about 1 A. In an embodiment, the time averaged current drawn from the battery is dependent upon the frequency at which the lens makes focal length changes. The controller 250 can include a capacitor (not shown) operably coupled to the battery and configured to deliver a specific voltage such as any of those described above, or higher values by use of voltage boosting circuitry. Suitable capacitors can include thin film capacitors. The controller 250 can include voltage booster circuitry, configured to increase the voltage supplied by the battery to a higher voltage in order to increase the bias voltage applied to a capacitor or to the electrodes of the diffractive lens (and hence to the electric field acting on an electro-optically active material within the diffractive lens). The power source 252 may include a parasitic power device, such as an induction coil, thermoelectric device, or any other device configured to harvest energy from a subject. In an embodiment the power source 252 can include a sufficiently small thermoelectric device (e.g., thermoelectric generator) configured to charge a battery or capacitor via heat harvested through the thermoelectric device. In an embodiment, the power source 252 can include an induction coil configured to produce current from a changing magnetic field applied thereto. For example, the induction coil can include a channel having a magnet therein, the channel passing the induction coil upon movement of the subject (e.g., eye-movement or blinking) In an embodiment, an induction coil can be disposed in the eye of a subject (e.g., in or adjacent to the IOL) and a corresponding magnet may be positioned on an adjacent part of the subject (e.g., an eyelid or bridge of the nose) whereby movement of the eye or eyelid can cause a current in the induction coil. The power source 252 can include one or more photocells configured to harvest optical energy received either from ambient lighting or from an artificial or user-directed light source. The induction coil, photocell, or thermoelectric device can be configured to charge a battery or capacitor, and can be configured to utilize voltage booster electrical circuitry. The power source 252 can include any other suitably sized device capable of providing an electrical charge.

The control electrical circuitry 254 can be coupled to the power source 252 and optionally include one or more gates or switches configured to selectively permit the power source 252 to apply a bias to one or more electrodes coupled thereto. The gates or switches can include an RF switch or a microwave switch by way of example. The control electrical circuitry 254 can include an antenna (e.g., RF or microwave antenna) or another means of receiving a signal from an activation source, such as a remote control device (not shown) wirelessly coupled to the controller 250. Each or the one or more switches or gates can be configured to open or close only upon receipt of a specific stimulus, such as a specific radio frequency signal or a specific microwave frequency signal. In an embodiment, the controller 250 can include two separate circuits operably coupled to the power source 252 and the control electrical circuitry 254, wherein a first circuit includes a switch configured to be actuated upon receiving a first radio frequency and a second circuit is configured to be actuated upon receiving a different, second radio frequency. Upon receipt of the specific radio frequency a switch can open or close. In an embodiment, one or more gates or switches can be located between the power source 252 and the control electrical circuitry 254, between the power source 252 and the electrical leads 256, or between the control electrical circuitry 254 and electrical leads 256.

In an embodiment, one or more of the controller 250, the power source 252, the control electrical circuitry 254, any other component of the controller 250, or at least a portion of one or more of the electrical leads 256 can be at least partially embedded within the haptic of an IOL. In an embodiment, an IOL system can include an activation source (not shown) such as a RF or microwave signal generator configured to selectively provide an activation stimulus or signal effective to direct the controller 250 (or a component thereof) to apply a bias across one or more electrodes. In an embodiment, the controller 250 can include a sensor configured to automatically detect if a different focal length is needed and responsive thereto, automatically direct the control electrical circuitry 254 or power source 252 to apply an electrical bias to one or more electrodes operably couple therewith. Such sensors can include one or more magnetic sensors configured to sense the point of focus through the alignment of magnetic markers in each eye of subject, a sensor configured to determine alignment of the eyes via relationship to a reference point remote from the subject, a sensor to determine a force applied by the eye's ciliary muscle (e.g., to the IOL's haptic), a sensor to determine the range to an object being observed via the IOL, or the like.

In an embodiment, the IOL system 200 can include one or more sensors configured to detect one or more physiological indicia. For example, the IOL system can include one or more physiological sensors configured to detect a physiological parameter in the eye of a subject such as glucose concentration, eye (e.g., intraocular) pressure, heart rate, biological proteins present in the eye, or any other biological indicia. The one or more sensors can be operably coupled to the controller 250. The controller 250 of the IOL system 200 may be configured to transmit the measurements of the physical indicia to a remote source such as a computer, a cellular phone, or other electronic device. In some embodiments, the measured physical indicia may be used to determine the health of a subject or eye thereof (e.g., determine if a subject is suffering from Glaucoma), customize the operation of the IOL to the particular subject, determine if the IOL needs to be removed or adjusted, or determine if the focal adjustments of the IOL are suitable for the subject. The electronic device may then transmit instructions to the controller 250 to selectively control or otherwise adjust the functioning of the IOL, responsive to the sensed physical indicia. While shown connected to the single diffractive lens 202, the controller 250 or second controller 250 can be operably coupled to at least one more diffractive lens in a similar or identical manner as disclosed above with reference to FIG. 7. In any event, the controller can be used to selectively change the focal length of the associated lens system to one or more alternative focal lengths. Any of the IOLs, diffractive lenses, or haptics herein can include a protective coating over at least a portion thereof sufficient to limit or prevent any materials or electrical bias from harming or unintentionally altering the surrounding tissue of the eye. Suitable protective coatings can include any of those materials known to be stable and inert when implanted in a subject such as a mammal (e.g., human).

FIGS. 8A and 8B are schematic side, cross-sectional views of an IOL system 800 before and after a bias is applied between the electrodes therein, respectively, according to an embodiment. Methods of modifying a focal length of an IOL system can include providing an IOL system, such as any described IOL system or component herein, and biasing at least some of the electrodes therein to modify an index of refraction of one or more materials therebetween. The IOL system 800 can include one or more diffractive lenses, such as diffractive lens 202. The diffractive lens 202 can be configured similarly or identical to any diffractive lens herein, such as a diffractive lens including at least one material 210 or 220 therein having an electrically-modifiable index of refraction (e.g., electro-optical material), one or more electrodes 218 or 228, and a control system (not shown) configured to provide an electrical bias between the one or more electrodes 218 and 228. The at least one material 210 or 220 can be similar or identical to any of the first or second materials herein, including any surfaces, compositions, shapes, or other properties associated therewith. The one or more electrodes 218 or 228 can be similar or identical to any first or second electrode herein, including any surfaces, compositions, positions, shapes, or other properties associated therewith. The IOL system 800 can include a controller 250 similar or identical to any controller disclosed herein, including any components, circuits, or configurations thereof. The controller 250 can include a circuit including one or more of the power source, the control electrical circuitry, and the first and second electrodes 218 and 228.

In a ground or inactive state shown in FIG. 8A, the circuit can be open, such that no bias is applied between the electrodes 218 and 228. In the ground state, the IOL system 800 exhibits a first focal length F1. In the ground or inactive state, light passing through the diffractive lens 202 can be focused onto the retina 129 of a subject having the IOL system 800 implanted therein. In certain instances, a subject may not be able to focus at a second focal length F2 without assistance. In such instances, a bias can be selectively applied to between the first and second electrodes 218 and 828, effective to modify the index of refraction of one or more electro-optical materials therebetween (e.g., the first material 210 or the second material 220). In an embodiment, a method of modifying a focal length of the IOL system 200 can include, via the controller 250, biasing the first and second electrodes to modify the index of refraction of one or more electro-optical materials therein. In an embodiment, a method of modifying a focal length of the IOL system 800 can include, via the controller 250, biasing the first and second electrodes to modify the index of refraction of a first electro-optical material and a second electro-optical material therein. In an embodiment, biasing the first and second electrodes 218 and 228 can include biasing the first and second electrodes 218 and 228 for a fixed amount of time. The fixed amount of time can be programmed into control electrical circuitry (or memory associated therewith) or be determined by the length of time that a stimulus is applied to the controller from an activation source (e.g., remote source of RF radiation). Suitable fixed times can include 30 seconds or more, such as 1 minute to 2 hours, 5 minutes to 1 hour, 10 minutes to 30 minutes, more than 10 minutes, less than 5 minutes, or more than 1 hour. In an embodiment, biasing the first and second electrodes 218 and 228 can include biasing the first and second electrodes 218 and 228 for an amount of time determined by the time for which the modified focal length is desired.

As shown in FIG. 8B, upon activation of the controller 250, the circuit including the controller 250 and the first and second electrodes 218 and 228 is closed thereby biasing the first and second electrodes 218 and 228 and the material therebetween. Upon biasing the first and second electrodes 218 and 228, the index of refraction of at least the electro-optical material in the first material 210 can be electrically modified to induce a modified index of refraction and the IOL system 800 can exhibit the second focal length F2. In an embodiment, the diffractive lens 202 can be configured such that the first focal length F1 can be greater than the second focal length F2. In an embodiment, the diffractive lens 202 can be configured such that the second focal length F2 can be greater than first focal length F1. In an embodiment, a refractive lens can be used optically in series with the diffractive lens 202, similar or identical to that shown in FIG. 3. In an embodiment, an IOL system can include at least one additional diffractive lens in series with the first diffractive lens similar or identical to those shown in FIGS. 4 and 5. In such embodiments, more than 2 focal lengths can be obtained by selectively applying a bias to one or more electrodes associated therewith.

FIG. 9 is a schematic side, cross-sectional view of an IOL system 900, according to an embodiment. The IOL system 900 can include more than one diffractive lens therein. The IOL system 900, or portions thereof, can be configured similarly or identical to the IOL systems shown in FIGS. 4 and 5. For example the IOL system 900 can include a first diffractive lens 202 and a second diffractive lens 204. The first diffractive lens 202 and a second diffractive lens 204 can be similar or identical to those diffractive lenses 202 and 204 described with respect to FIGS. 4 and 5, including any portions of components thereof. For example, the first diffractive lens 202 can include the first material 210 and the second material 220, and the second diffractive lens 204 can include the third material 230 and the fourth material 240, as described above. The IOL system 900 can include a plurality of electrodes 218-248. For example, the first electrode 218 can be disposed adjacent to the first material 210, the second electrode 228 can be positioned adjacent to the second material 220, the third electrode 238 can be positioned adjacent to the third material 230 or the fourth material 240, and the fourth electrode 248 can be positioned adjacent to the fourth material 240. The electrodes 218, 228, 238 and 248 can be similar or identical to those described above with reference to FIGS. 4 and 5. The IOL system 900 can include one or more controllers 250 operably coupled to one or more of the electrodes 218-248. The one or more controllers 250 can be configured or positioned in any manner disclosed herein, such as those described above with reference to FIGS. 4 and 5.

In an embodiment, none of the diffractive lenses 202 or 204; the first diffractive lens 202; the second diffractive lens 204; or both diffractive lenses 202 and 204 can be selectively biased, thereby altering the index of refraction of one or more electro-optical materials therein and the focal length of the IOL system 900. The IOL system 900 having the first diffractive lens 202 and the second diffractive lens 204 can include four selectively controllable focal lengths. For example, the first diffractive lens 202 can include one or more materials having an electrically-modifiable index of refraction and the second diffractive lens 204 can include one or more materials having an electrically-modifiable index of refraction. The electrodes 218-248 individually associated therewith can be selectively biased to alter only one of, or both of, the indices of refraction of the electro-optical materials in the first diffractive lens 202 or the second diffractive lens 204. In a ground or inactive state, the IOL system 900 can exhibit a first focal length F1. In an embodiment, the first and second electrodes 218 and 228 can be biased to modify the index of refraction of one or both of the first or second materials 210 or 220 in the diffractive lens 202. Upon application of the bias to the first and second electrodes 218 and 228 by the controller 250, the index of refraction of at least one of the electro-optical materials in the first diffractive lens (e.g., first material 210 or second material 220) can be modified and the IOL system 900 can exhibit a second focal length F2.

In an embodiment, the IOL system 900 can include the second diffractive lens 204 having the third and fourth electrodes 238 and 248 disposed adjacent to the third and fourth materials 230 and 240 respectively, as shown in FIG. 9. In an embodiment, modifying the focal length of the IOL system 900 can include selectively biasing the third and fourth electrodes 238 and 248 to change the index of refraction of one or both of the third or fourth materials 230 and 240. Upon application of the bias to third and fourth electrodes 238 and 248 by the controller 250, the index of refraction of one or more electro-optical materials in the second diffractive lens 204 can be modified and the IOL system 900 can exhibit a third focal length F3. In an embodiment, modifying the focal length of the IOL system 900 can include selectively biasing one or both of the first and second electrodes 218 and 228 or the third and fourth electrodes 238 and 248 to change the index of refraction of one or more of the first, second, third, or fourth materials 210-240, respectively associated therewith. In an embodiment, modifying the focal length of the IOL system 900 can include selectively biasing one the first and second electrodes 218 and 228, or the third and fourth electrodes 238 and 248, at a time. In an embodiment, modifying the focal length of the IOL system 900 can include selectively biasing both of first and second electrodes 218 and 228 and the third and fourth electrodes 238 and 248 substantially simultaneously. In an embodiment, modifying the focal length of an IOL can include providing an activation signal to the controller 250, such as from an activation source (e.g., remote RF signal generator). The activation signal can include instructions effective to bias one or more of the first and second electrodes 218 and 228; or the third and fourth electrodes 238 and 248.

In an embodiment, modifying the focal length of an IOL can include biasing all of the electrodes 218-248, wherein the electrically-modifiable index of refraction of one or more materials 210-240 in each of the first diffractive lens 202 and the second diffractive lens 204 can be modified to alter the focal length of the IOL system 900 to provide a fourth focal length F4. The controller 250 can be configured to selectively bias one or more of the electrodes 218-248. In an embodiment, a refractive lens can be placed in series with the diffractive lenses 202 and 204, such as described above with reference to FIG. 5.

In an embodiment, the IOL system 900 can include the second diffractive lens 204 having the third electrode 238 disposed adjacent to one of the third or fourth materials 230 or 240 and the opposite side of the diffractive lens 204 can be placed adjacent to the first electrode 218 or the second electrode 228, substantially as shown in and described with respect to FIG. 4. In an embodiment of a method of modifying the focal length of the IOL system 900, the third electrode 238 and one of the first or second electrodes 218 or 228 can be selectively biased using the controller 250 to selectively change the index of refraction of one or both of the third or fourth materials 230 and 240. Upon application of a bias to the third electrode 238 and one of the first or second electrodes 218 or 228 by the controller 250, the index of refraction of one of the electro-optical materials in the second diffractive lens 204 can be modified and the IOL system 900 can exhibit the third focal length F3.

In an embodiment, modifying the focal length of an IOL can include biasing all of the electrodes 218-238, wherein the electrically-modifiable index of refraction of one or more materials 210-240 in each of the first diffractive lens 202 and the second diffractive lens 204 can be modified to alter the focal length of the IOL system 900 to provide the fourth focal length F4. The controller 250 can be configured to selectively bias one or more of the electrodes 218-238. The shared electrode 218 or 228 between the first diffractive lens 202 and the second diffractive lens 204 can be operably connected to two circuits having separately controlled gates or switches capable of selectively providing a bias to only a single set of electrodes at a time or both sets of electrodes substantially simultaneously. In an embodiment, a refractive lens can be placed in series with the diffractive lenses 202 and 204, such as described above with reference to FIG. 5.

In an embodiment, the first focal length F1 associated with the inactive state of the first and second diffractive lenses 202 and 204 (e.g., unbiased electrodes corresponding to unaltered indices of refraction in the materials therein) can be greater than one or more of the second focal length F2, the third focal length F3, or the fourth focal length F4.

In an embodiment, the second focal length F2 associated with the active state of the first diffractive lens 202 can be greater than the third focal length F3 or the fourth focal length F4. (e.g., electrically biased state of the electro-optical material inducing an electrically-modified index of refraction in one or more of the first or second materials 210 or 220)

In an embodiment, the third focal length F3 associated with the active state of the second diffractive lens 204 can be greater than the fourth focal length F4. In an embodiment, the third focal length F3 can be greater than the second focal length F2. In an embodiment, the method of modifying the focal length of an IOL can include, via the controller 250, biasing the third electrode 238 and the fourth electrode 248 to modify at least the electrically-modifiable third index of refraction of the third material 230 and the focal length of the IOL system 900 to achieve the third focal length F3.

In an embodiment, the method of modifying the focal length of an IOL further includes, via the controller 250, biasing the third electrode 238 and the one of the first or second electrodes 218 or 228 to modify at least the electrically-modifiable third index of refraction of the third material 230 and the focal length of the IOL system 900 to achieve the third focal length F3. In an embodiment, biasing the third electrode 238 and the one of the first or second electrodes 218 or 228 can include selectively biasing only one of: the first and second electrodes 218 and 228; or the third electrode 238 and the one of the first or second electrodes 218 or 228, at a time. In an embodiment, biasing the third electrode 238 and the one of the first or second electrodes 218 or 228 can include selectively biasing both of the first and second electrodes 218 and 228; and the third electrode 238 and the one of the first or second electrodes 218 or 228, substantially simultaneously. In an embodiment, modifying the focal length of an IOL can include providing an activation signal to the controller 250, such as from an activation source. The activation signal can include instructions effective to or cause the controller 250 to bias one or more of the first and second electrodes 218 and 228; or the third and electrode 238 and one of the first electrode 218 or the second electrode 228.

In an embodiment, the fourth focal length F4 associated with the active state for both the first and second diffractive lenses 202 and 204 can be less than one or more of the first focal length F1, the second focal length F2, or the third focal length F3.

In an embodiment, modifying the focal length of an IOL can include determining a selected focal length. Determining a selected focal length can include determining a selected focal length based on an activity such as reading, watching television or a live performance, playing a sport, or any other activity. A selected focal length can be programmed into the controller 250 corresponding to a specific activity and can be selectively induced by biasing one or more electrodes in an IOL based on participation in the activity. In an embodiment, biasing the one or more of the first and second electrodes 218 and 228 or the third and fourth electrodes 238 and 248 to modify at least the electrically-modifiable first index of refraction of one or more of the first, second, third, or fourth materials 210-240 and a focal length of the intraocular lens system 900 includes selectively biasing one or more of the first and second electrodes 218 or 228 or the third and fourth electrodes 238 or 248 responsive to the selected focal length.

In an embodiment, modifying the focal length of an IOL can include providing an IOL having at least one electro-optical material having a plurality of tunable focal lengths (e.g., collectively forming a gradient), each focal length being dependent upon the amount of voltage applied to the electro-optical material. For example, an IOL having a plurality of tunable focal lengths can include a first, electro-optical material having a Fresnel lens configuration, and a second, electro-optical or inert material having a complementary geometry to the first electro-optical material. The Fresnel lens blazing can be configured to focus one or more of a plurality of orders of light onto the retina of a subject, each order being induced by a change in the refractive properties of the first electro-optical material due to a specific electrical bias. Each individual order of light of the plurality of orders of light can be focused by inducing a specific voltage at the electro-optical material(s). The individual orders of light can be gradually changed from one to another, thereby allowing a tunable gradient of focal lengths. In an embodiment, the second material can be configured as a Fresnel lens, and the first material can exhibit complementary surface geometry to the second material such that an interface between the two materials is substantially seamless. In such an embodiment, the first material may be inert or an electro-optical material and the second material may be an electro-optical material the same as or different than the first electro-optical material. The IOL systems having the same may be substantially similar to or identical to any IOL system disclosed herein, including one or more components thereof.

Modifying the focal length of the IOL having a plurality of tunable focal lengths can include gradually adjusting the electrical bias to the first and second electrodes until a desired focal length is reached. The desired focal length can be between a maximum focal length of the inactive IOL and the minimum focal length of the fully biased IOL (e.g., biased to the fullest extent of the power source or materials therein). Gradually adjusting the electrical bias can include gradually increasing or decreasing the electrical bias to gradually increase or decrease the focal length of the IOL.

In an embodiment, modifying the focal length of an IOL can include providing an IOL, such as any IOL described herein. In an embodiment, modifying the focal length of an IOL can include positioning an IOL within the eye of a subject. Positioning an IOL within the eye of a subject can include surgically implanting an IOL in the eye of a subject.

It will be understood that a wide range of hardware, software, firmware, or virtually any combination thereof can be used in the controllers described herein. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more programs running on one or more processors (e.g., as one or more programs running on one or more microprocessors), as firmware, or as virtually any combination thereof. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, or virtually any combination thereof and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" or "adapted to" are synonymous and can generally encompass active-state components and/or inactive-state components and/or standby-state components, unless context requires otherwise.

While particular aspects of the present subject matter described herein have been shown and described, it will be apparent that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, any recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. An intraocular lens system, comprising:
   a diffractive lens configured to be implanted in an eye of a subject, the diffractive lens including,
      a first material having,
         an electrically-modifiable first index of refraction;
         a first outer surface; and
         a first diffraction surface defining a first diffraction pattern;
      a second material having,
         a second index of refraction;
         a second outer surface remote from and generally opposing the first outer surface of the first material; and
         a second diffraction surface defining a second diffraction pattern, wherein the second diffraction pattern is substantially complementary to the first diffraction pattern;
   a first electrode disposed adjacent to the first outer surface of the first material;
   a second electrode disposed adjacent to the second outer surface of the second material, at least one of the first material or the second material including an electro-optical material, and the second material includes an electrically-modifiable second index of refraction; and
   a controller including control electrical circuitry operably coupled to the first and second electrodes, the controller configured to bias the first and second electrodes to modify at least the electrically-modifiable first index of refraction of the first material and a focal length of the intraocular lens system.

2. The intraocular lens system of claim 1, wherein the first material and the second material have substantially the same DC dielectric constant.

3. The intraocular lens system of claim 1, wherein the at least one of the first material or the second material includes at least one of lithium niobate, lithium tantalate, lead zirconate titanate, potassium dihydrogen phosphate, or cadmium telluride.

4. The intraocular lens system of claim 1, wherein the at least one of the first material or the second material includes a solid state electro-optical material.

5. The intraocular lens system of claim 1, wherein the at least one of the first material or the second material includes a liquid crystal.

6. The intraocular lens system of claim 1, wherein the first material includes an electro-optical material and the second material includes an electro-optical material.

7. The intraocular lens system of claim 6, wherein the electro-optical material of the first and second materials includes at least one of lithium niobate, lithium tantalate, lead zirconate titanate, potassium dihydrogen phosphate, or cadmium telluride.

8. The intraocular lens system of claim 6, wherein the electro-optical material of the first and second materials includes a solid state electro-optical material.

9. The intraocular lens system of claim 6, wherein the electro-optical material of the first and second materials includes a liquid crystal.

10. The intraocular lens system of claim 1, further comprising a refractive lens having a substantially fixed index of refraction, the refractive lens disposed optically in series with the diffractive lens.

11. The intraocular lens system of claim 10, wherein the refractive lens is positioned proximate to the first outer surface of the first material or the second outer surface of the second material.

12. The intraocular lens system of claim 11, wherein one surface of the refractive lens is positioned adjacent either to the first electrode or to the second electrode.

13. The intraocular lens system of claim 1, further comprising a refractive lens is formed by the second material and one surface of the refractive lens is positioned adjacent to the second electrode.

14. The intraocular lens system of claim 1, wherein each of the first electrode and the second electrode is substantially planar.

15. The intraocular lens system of claim 1, wherein the first outer surface of the first material and the second outer surface of the second material are substantially parallel.

16. The intraocular lens system of claim 1, wherein each of the first outer surface of the first material and the second outer surface of the second material is substantially planar.

17. The intraocular lens system of claim 1, wherein the first outer surface of the first material and the second outer surface of the second material have a substantially identical curvature.

18. The intraocular lens system of claim 1, wherein the first outer surface of the first material and the second outer surface of the second material have different curvatures, and wherein the difference in curvatures defines a refractive lens.

19. The intraocular lens system of claim 18, further comprising an interface between the first material and the second material that includes a substantially identical curvature as the second outer surface of the second material.

20. The intraocular lens system of claim 18, further comprising an interface between the first material and the second material that includes a substantially identical curvature as the first outer surface of the first material.

21. The intraocular lens system of claim 1, wherein each of the first and second electrodes is substantially transparent to visible wavelength light.

22. The intraocular lens system of claim 1, wherein the diffractive lens has a first focal length when the first and second electrodes are not biased and a second focal length when the first and second electrodes are biased.

23. The intraocular lens system of claim 22, wherein the first focal length is greater than the second focal length.

24. The intraocular lens system of claim 1, wherein the first diffraction pattern and second diffraction pattern define a Fresnel lens.

25. The intraocular lens system of claim 1, wherein the first diffraction pattern is defined by a thickness variation of the first material.

26. The intraocular lens system of claim 1, wherein the second diffraction pattern is defined by a thickness variation of the second material.

27. The intraocular lens system of claim 1, wherein the first diffraction pattern and the second diffraction pattern have substantially identical spatial periodicity.

28. The intraocular lens of claim 1, further comprising at least one additional diffractive lens in series with the diffractive lens.

29. The intraocular lens system of claim 28, wherein:
the at least one additional diffractive lens includes,
a third material having,
an electrically-modifiable third index of refraction;
a third outer surface; and
a third diffraction surface defining a third diffraction pattern;
a fourth material having,
a fourth index of refraction;
a fourth outer surface remote from and generally opposing the third outer surface of the third material; and
a fourth diffraction surface defining a fourth diffraction pattern, wherein the fourth diffraction pattern is substantially complementary to the third diffraction pattern;
the intraocular lens system includes,
a third electrode disposed adjacent to the fourth outer surface of the fourth material and operably coupled to the controller;
one of the first or second electrodes disposed adjacent to the third outer surface of the third material; and
wherein the controller is configured to bias the third and the one of the first or second electrodes to alter the electrically-modifiable third index of refraction of the third material.

30. The intraocular lens system of claim 29, further comprising a refractive optical element in series with the diffractive lens and the additional diffractive lens.

31. The intraocular lens system of claim 28, wherein:
the additional diffractive lens includes,
a third material having,
an electrically-modifiable third index of refraction;
a third outer surface; and
a third diffraction surface defining a third diffraction pattern;
a fourth material having,
a fourth index of refraction;
a fourth outer surface remote from and generally opposing the third outer surface of the third material; and
a fourth diffraction surface defining a fourth diffraction pattern, wherein the fourth diffraction pattern is substantially complementary to the third diffraction pattern;
the intraocular lens system includes,
a third electrode disposed adjacent to the third outer surface of the third material and operably coupled to the controller;
a fourth electrode disposed adjacent to the fourth outer surface of the fourth material and operably coupled to the controller; and
the controller is configured to bias the third and fourth electrodes to alter the electrically-modifiable third index of refraction of the third material and the focal length of the intraocular lens system.

32. A method of modifying a focal length of an intraocular lens, the method comprising:
wherein the intraocular lens includes a diffractive lens having,
a first material having,
an electrically-modifiable first index of refraction;
a first outer surface; and
a first diffraction surface defining a first diffraction pattern;
a second material having,
a second index of refraction;
a second outer surface remote from and generally opposing the first outer surface of the first material; and
a second diffraction surface defining a second diffraction pattern, wherein the second diffraction pattern is substantially complementary to the first diffraction pattern;
a first electrode disposed adjacent to the first outer surface of the first material;
a second electrode disposed adjacent to the second outer surface of the second material that includes an electrically-modifiable second index of refraction;

a controller including control electrical circuitry operably coupled to the first and second electrodes, the controller configured to bias the first and second electrodes to modify at least the electrically-modifiable index of refraction of the first material and a focal length of the diffractive lens; and via the controller, biasing the first and second electrodes to modify at least the electrically-modifiable first index of refraction of the first material.

33. The method of claim 32, wherein each of the first and second electrodes is substantially transparent to visible wavelength light.

34. The method of claim 32, wherein the intraocular lens includes a refractive lens having a substantially fixed index of refraction, the refractive lens optically in series with the diffractive lens.

35. The method of claim 34, wherein one surface of the refractive lens is positioned adjacent to the first electrode or to the second electrode.

36. The method of claim 35, wherein biasing the first and second electrodes to modify at least the electrically-modifiable first index of refraction of the first material and the focal length of the intraocular lens includes biasing the first and second electrodes for a selected amount of time.

37. The method of claim 32, further comprising a refractive lens is formed by the second material and one surface of the refractive lens is positioned adjacent to the second electrode.

38. The method of claim 32, wherein biasing the first and second electrodes to modify at least the electrically-modifiable first index of refraction of the first material includes biasing the first and second electrodes to modify the electrically-modifiable first index of refraction of the first material and an electrically-modifiable second index of refraction of the second material.

39. The method of claim 32, wherein biasing the first and second electrodes to modify at least the electrically-modifiable first index of refraction of the first material and the focal length of the intraocular lens includes biasing the first and second electrodes for a selected amount of time.

40. The method of claim 32, wherein the first outer surface of the first material and the second outer surface of the second material are substantially parallel.

41. The method of claim 32, wherein each of the first outer surface of the first material and the second outer surface of the second material is substantially planar.

42. The method of claim 32, wherein the second outer surface of the second material includes a curvature and the first outer surface includes a substantially identical curvature to the second outer surface of the second material.

43. The method of claim 32, wherein the first outer surface of the first material and the second outer surface of the second material have different curvatures, the difference in curvatures defining a refractive lens.

44. The method of claim 32, wherein the intraocular lens includes an additional diffractive lens in series with the diffractive lens.

45. The method of claim 44, wherein:
the additional diffractive lens includes,
a third material having,
an electrically-modifiable third index of refraction;
a third outer surface; and
a third diffraction surface defining a third diffraction pattern;
a fourth material having,
a fourth index of refraction;
a fourth outer surface remote from and generally opposing the third outer surface of the third material; and
a fourth diffraction surface defining a fourth diffraction pattern, wherein the fourth diffraction pattern is substantially complementary to the third diffraction pattern;
the intraocular lens includes,
a third electrode disposed adjacent to the fourth outer surface of the fourth material and operably coupled to the controller;
one of the first or second electrodes disposed adjacent to the third outer surface of the third material; and
the method further includes, via the controller, biasing the third and the one of the first or second electrodes to modify at least the electrically-modifiable third index of refraction of the third material and the focal length of the intraocular lens.

46. The method of claim 45, wherein biasing the third and the one of the first or second electrodes includes selectively biasing only one of: the first and second electrodes; or the third and the one of the first or second electrodes at a time.

47. The method of claim 45, wherein biasing the first and second electrodes and biasing the third and the one of the first or second electrodes includes substantially simultaneously biasing the first and second electrodes and the third and the one of the first or second electrodes.

48. The method of claim 45, further comprising providing an activation signal to the controller, the activation signal including instructions effective to bias one or more of the first and second electrodes or the third and fourth electrodes.

49. The method of claim 44, wherein the intraocular lens includes a refractive optical element positioned in series with the diffractive lens and the additional diffractive lens.

50. The method of claim 44, wherein:
the additional diffractive lens includes,
a third material having,
an electrically-modifiable third index of refraction;
a third outer surface; and
a third diffraction surface defining a third diffraction pattern;
a fourth material having,
a fourth index of refraction;
a fourth outer surface remote from and generally opposing the third outer surface of the third material; and
a fourth diffraction surface defining a fourth diffraction pattern, wherein the fourth diffraction pattern is substantially complementary to the third diffraction pattern;
the intraocular lens includes,
a third electrode disposed adjacent to the fourth outer surface of the fourth material and operably coupled to the controller;
a fourth electrode disposed adjacent to the fourth outer surface of the fourth material and operably coupled to the controller; and
the method further comprising, via the controller, biasing the third and fourth electrodes to modify at least the electrically-modifiable third index of refraction of the third material and the focal length of the intraocular lens.

51. The method of claim 50, wherein biasing the first and second electrodes and biasing the third and the fourth electrodes includes selectively biasing only one of: the first and second electrodes; or the third and fourth electrodes at a time.

52. The method of claim 32, wherein biasing the first and second electrodes to modify at least the electrically-modifiable first index of refraction of the first material includes providing an activation signal to the controller effective to bias the first and second electrodes.

53. The method of claim 32, wherein the intraocular lens comprises a refractive optical element positioned in series with the diffractive lens.

54. The method of claim 32, further comprising determining a selected focal length; and
wherein biasing the first and second electrodes to modify at least the electrically-modifiable first index of refraction of the first material and a focal length of the intraocular lens includes selectively biasing the first and second electrodes responsive to the selected focal length.

55. The intraocular lens system of claim 1, wherein each of the first and second diffraction surfaces includes a pattern of peaks and valleys.

56. The intraocular lens system of claim 32, wherein each of the first and second diffraction surfaces includes a pattern of peaks and valleys.

57. An intraocular lens system, comprising:
a diffractive lens configured to be implanted in an eye of a subject, the diffractive lens including,
a first material having,
an electrically-modifiable first index of refraction;
a first outer surface; and
a first diffraction surface defining a first diffraction pattern;
a second material having,
a second index of refraction;
a second outer surface remote from and generally opposing the first outer surface of the first material; and
a second diffraction surface defining a second diffraction pattern, wherein the second diffraction pattern is substantially complementary to the first diffraction pattern, and the first material and the second material have substantially the same DC dielectric constant;
a first electrode disposed adjacent to the first outer surface of the first material;
a second electrode disposed adjacent to the second outer surface of the second material; and
a controller including control electrical circuitry operably coupled to the first and second electrodes, the controller configured to bias the first and second electrodes to modify at least the electrically-modifiable first index of refraction of the first material and a focal length of the intraocular lens system.

* * * * *